(12) United States Patent
O'Leary et al.

(10) Patent No.: US 9,457,117 B2
(45) Date of Patent: Oct. 4, 2016

(54) EMANATOR ELEMENT FOR VOLATILE LIQUIDS AND DEVICES INCORPORATING SAME

(75) Inventors: Nicholas O'Leary, Pennington, NJ (US); David Granger, Syracuse, IN (US)

(73) Assignee: Firmenich SA, Geneva (CH)

( * ) Notice: Subject to any disclaimer, the term of this patent is extended or adjusted under 35 U.S.C. 154(b) by 251 days.

(21) Appl. No.: 13/981,665

(22) PCT Filed: Feb. 9, 2012

(86) PCT No.: PCT/EP2012/052230
§ 371 (c)(1),
(2), (4) Date: Jul. 25, 2013

(87) PCT Pub. No.: WO2012/107527
PCT Pub. Date: Aug. 16, 2012

(65) Prior Publication Data
US 2013/0306753 A1  Nov. 21, 2013

Related U.S. Application Data

(60) Provisional application No. 61/441,159, filed on Feb. 9, 2011.

(51) Int. Cl.
*A61L 9/12* (2006.01)
*F24F 3/16* (2006.01)

(52) U.S. Cl.
CPC .................. *A61L 9/122* (2013.01); *A61L 9/12* (2013.01); *A61L 9/127* (2013.01); *F24F 2003/1689* (2013.01)

(58) Field of Classification Search
CPC .......... A61L 9/12; A61L 9/122; A61L 9/127
See application file for complete search history.

(56) References Cited

U.S. PATENT DOCUMENTS

| | | | | | |
|---|---|---|---|---|---|
| 1,323,462 | A | * | 12/1919 | Flanders | 422/124 |
| 1,911,871 | A | * | 5/1933 | Andersen | 422/124 |
| 2,164,763 | A | * | 7/1939 | Buck | 261/30 |

(Continued)

FOREIGN PATENT DOCUMENTS

WO    WO2004/006968 A1    1/2004

OTHER PUBLICATIONS

International Search Report and Written Opinion, application PCT/EP2012/052230, mailed Apr. 26, 2012.

*Primary Examiner* — Ryan Reis
(74) *Attorney, Agent, or Firm* — Winston & Strawn LLP

(57) ABSTRACT

An assembly for evaporation and dispensing of a volatile liquid. The assembly includes an emanator element and a body member. The emanator element has an open structure with a high surface area and is made of a material that is able to absorb and evaporate volatile liquids. The body member includes a tubular portion which has an interior wall for receiving the emanator element, the latter possibly being therein spaced from the interior wall to allow air flow therethrough. A reservoir of volatile liquid and a wicking member are also provided with the wicking element extending from the emanator element into the volatile liquid. The assembly is further associated with an air moving component for directing air flow though the tubular portion and around and through the open structure of the emanator element, thus carrying evaporated liquid volatiles out of the body member.

20 Claims, 15 Drawing Sheets

(56) References Cited

U.S. PATENT DOCUMENTS

| | | | |
|---|---|---|---|
| 2,614,820 A * | 10/1952 | Boydjieff | 261/26 |
| 2,653,017 A * | 9/1953 | Frost | 261/72.1 |
| 4,148,849 A | 4/1979 | Steiner | |
| 5,662,835 A * | 9/1997 | Collingwood | 261/26 |
| 7,441,755 B2 | 10/2008 | O'Leary et al. | |
| 7,499,632 B2 * | 3/2009 | Granger et al. | 392/386 |
| 2006/0043619 A1 * | 3/2006 | Brown et al. | 261/19 |
| 2006/0076429 A1 | 4/2006 | Kvietok et al. | |
| 2007/0125874 A1 | 6/2007 | Alexander | |
| 2010/0044468 A1 | 2/2010 | Granger et al. | |

* cited by examiner

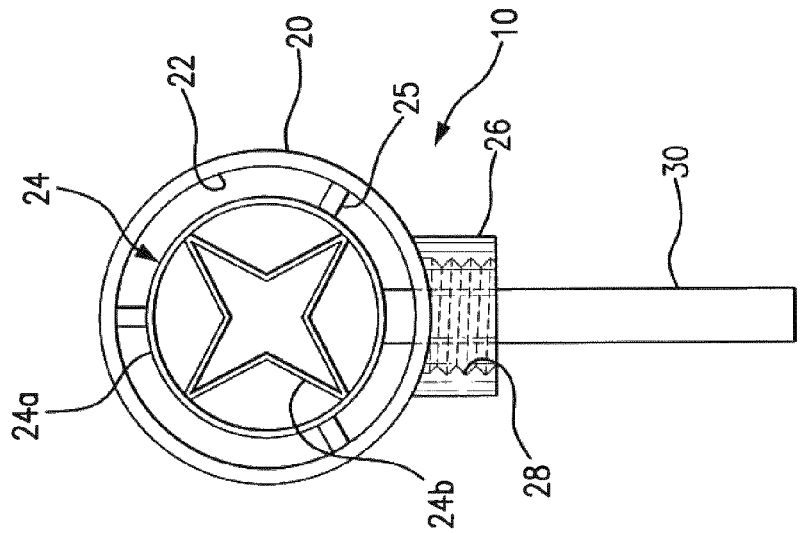
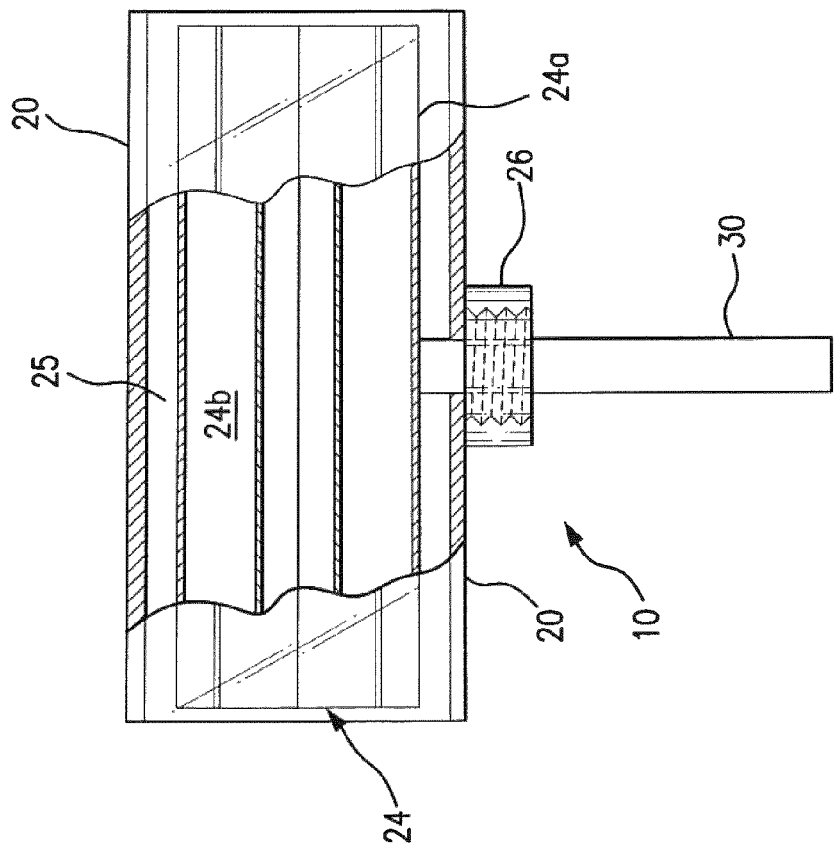

FIG. 11 - Cumulative Mass of Volatile Composition Released from the Device Described in Example 1.

FIG. 12 - Cumulative Mass of Volatile Composition Released from the Device Described in Example 2.

FIG. 13 – Cumulative Mass of Volatile Composition Released from the Device Described in Example 3.

FIG. 14 - Cumulative Mass of Volatile Composition Released from the Device Described in Example 4.

FIG. 15 - Cumulative Mass of Volatile Composition Released from the Device Described in Example 5.

EMANATOR ELEMENT FOR VOLATILE LIQUIDS AND DEVICES INCORPORATING SAME

TECHNICAL FIELD

The present invention relates to the field of perfumery and more precisely it concerns an assembly that includes an emanator element for evaporation and dispensing of an active volatile liquid into the surrounding space. The emanator element has a particular structure and is made of a material that receives and optimizes evaporation of the volatile liquid and is used with a reservoir or supply of the liquid. It also is preferably used in association with a device that includes a fan or blower to dispense the evaporated liquid in a controllable manner.

BACKGROUND

Devices for dispensing an active volatile liquid in the surrounding space have been known for a long time. One type device is the so-called wick-based device, which comprises a reservoir, a wick for absorbing the liquid in the reservoir and transporting it to the emanating body from which the active liquid evaporates.

The main problem of such wick-based devices is the difficulty to achieve a controlled release in the surroundings of the active liquid in order to avoid that the evaporation of the active liquid is too quick or too slow, and the control of a linear delivery, with the same olfactive quality over time, of the fragrance into the surroundings. Moreover, when used to impart a fragrance to a particular room, in combination with a heating element for example, the lack of control can lead to too much or too little fragrance dispensed into the room such that the fragrance is either not perceived or is too strong.

The various wick-based devices disclosed in the prior art can be divided in several categories. Each category is characterized by the fact that the device achieves a controlled release by:
i) the use of special films or occluding systems which enwrap the emanating body;
ii) the use of a cover to regulate, over the lifetime of the device, the surface of the emanating body from which the active liquid can evaporate (i.e., the evaporative surface); or
iii) the use of an electrically powered assistance such as heating or a fan.

These devices are complex to realize and require additional elements. Moreover, with the exception of the electrically assisted devices, the other devices require, in general, the use of an aqueous solution or emulsion of the active liquid, thus implying the use of large amounts of liquid and of surfactants which may be detrimental to the effective releasing performance of the device.

To try to resolve these problems, U.S. Pat. No. 7,441,755 discloses a non-electrically powered device comprising: a) a reservoir chamber having an open end; b) a non-aqueous active volatile liquid composition containing at least two ingredients; c) a reservoir chamber lid securely covering the open end of the reservoir chamber, the lid having at least one aperture; and d) a wick-emanator superstructure securely positioned in the aperture of the reservoir chamber lid. The superstructure includes I) an emitting part extending over the reservoir chamber lid and having an evaporative surface exposed to the surrounding air; and II) a wicking part extending down through the lid and in submerged contact with the active volatile liquid. This device is characterized in that i) at least 60% by weight of the non-aqueous active volatile liquid composition comprising ingredients having a vapor pressure of between 4 Pa and 270 Pa; ii) the emitting part has a weight of between 80 and 1000 grams per square meter of evaporative surface and an absorbency of between 0.01 and 0.1 grams of non-aqueous active volatile liquid composition per square centimeter of evaporative surface; and iii) less than about 20% by weight of the non-aqueous active volatile liquid composition is absorbed by the emitting part. This certainly increases the evaporative surface area, but is reliant upon the surrounding air to disperse the evaporated liquid.

U.S. Pat. No. 7,499,632 discloses a distribution device for distributing volatile fluids in air. In an exemplary embodiment, the distribution device includes a wick formed of a solid material which is impregnated with a volatile fluid, such as a scented liquid, a disinfectant, a fungicide, an anti-allergenic substance, an insect repellant, or an insecticide, for example. In another embodiment, the device includes a substantially hollow, tubular shaped wick which includes a portion that is exposed to the surrounding environment and a portion that is in liquid communication with a liquid reservoir containing a volatile fluid. The wick is positioned in the liquid reservoir and in a close fitting engagement with an open end of the liquid reservoir. The hollow configuration of the wick provides a greater exposed surface area to enhance the evaporation of the liquid into the surrounding environment. Even so, the resulting area, is relatively small such that the types of liquid that are suitable for us are those that are highly volatile. This limits that type and range of fragrances that can be dispensed by the device.

Accordingly, there remains a need in the art for improvements in this area. And these are now provided by the present invention.

SUMMARY OF THE INVENTION

The present invention relates to an assembly for evaporation and dispensing of a volatile liquid. The apparatus comprises an emanator element and a body member. The emanator element has an open structure with a high surface area and is made of a material that is able to absorb and evaporate volatile liquids. The body member includes a tubular portion which has an interior wall for receiving the emanator element therein. When the body member receives the emanator element, the emanator element can be spaced from the interior wall to allow air flow through the open emanator structure as well as between the interior wall and the emanator structure. Alternatively, all the air flow occurs through the open emanator structure and no space is provided between the interior wall of the body member tubular portion and the emanator element.

The tubular portion of the body member can be of any shape, provided it is adapted to receive the emanator element.

The body member of the assembly can also include a volatile fluid reservoir engaging portion surrounding a passage that extends from the engaging portion to the tubular portion. A wicking element can also be included, which extends away from the emanator element and at least into the reservoir engaging portion.

The emanator element of the assembly generally includes folds, corrugations, ripples, waves or other arrangements to maximize surface area in a minimum space, the evaporation of the volatile liquid occurring over the entire surface area of the emanator element. The emanator element can be made of cellulose filter paper, cellulose board, a non-woven material, a plastic or a porous or unglazed ceramic. In addition, the interior wall of the tubular portion can also include internal ribs or spacers to position the emanator element away from the interior wall to allow air flow between the wall and emanator element.

The invention also provides for a combination of one of the assemblies disclosed herein and a reservoir of a volatile liquid. This embodiment further comprises a wicking element extending from the emanator element into the volatile liquid and either being part of or associated with the emanator element or being associated with the reservoir. Additionally, one or more wicking elements can be present. The combination also optionally includes threads on the engaging portion for engaging mating threads of the reservoir.

Another embodiment of the invention relates to a device for evaporation and dispensing of a volatile liquid. The device comprises any one of the assembly or combination embodiments disclosed herein along with an air moving component for carrying evaporated liquid volatiles out of the body member. The air moving component is operatively associated with the assembly for directing air flow though the tubular portion and around and/or through the open structure of the emanator element. The air moving component can comprise a fan or blower which is controlled by a circuit board that provides on and off times such that the fan or blower is on and providing air movement for between 5% and 50% of the time.

The invention also provides a method of evaporating and dispensing of a volatile liquid from a reservoir by providing the assembly or combination of the embodiments disclosed herein, associating the wicking element with both the emanator element and the volatile liquid so that the volatile liquid is absorbed into and across the entire surface of the emanating element, and directing air flow though the tubular portion and around and/or through the open structure of the emanator element, preferably by the air moving component, for carrying evaporated liquid volatiles out of the body member.

The invention also relates to the use of an emanator element having an open structure and high surface area, and made of a material that is able to absorb and evaporate volatile liquids for evaporating and dispensing of a volatile liquid. The emanator element can be provided in a body member that includes a tubular portion having an interior wall. When received in the body member, the emanator element may be spaced from the interior wall to allow air flow through the open emanator structure as well as between the wall and the emanator structure. Alternatively, all the air flow occurs through the open emanator structure. The emanator element is operatively associated with a reservoir of volatile liquid and a wicking member. As above, the wicking element extends from the emanator element into the volatile liquid and is either part of or associated with the emanator element or is associated with the reservoir. The assembly is further associated with an air moving component for directing air flow though the tubular portion and around and through the open structure of the emanator element, thus carrying evaporated liquid volatiles out of the body member.

BRIEF DESCRIPTION OF THE DRAWINGS

FIG. 1 is a front view of an embodiment of the emanator element with folds that give it a four-pointed star cross section and attached to a wick.

FIG. 2 is a side cross sectional view of the assembly and combination of FIG. 1.

DETAILED DESCRIPTION OF THE INVENTION

Figure 3:
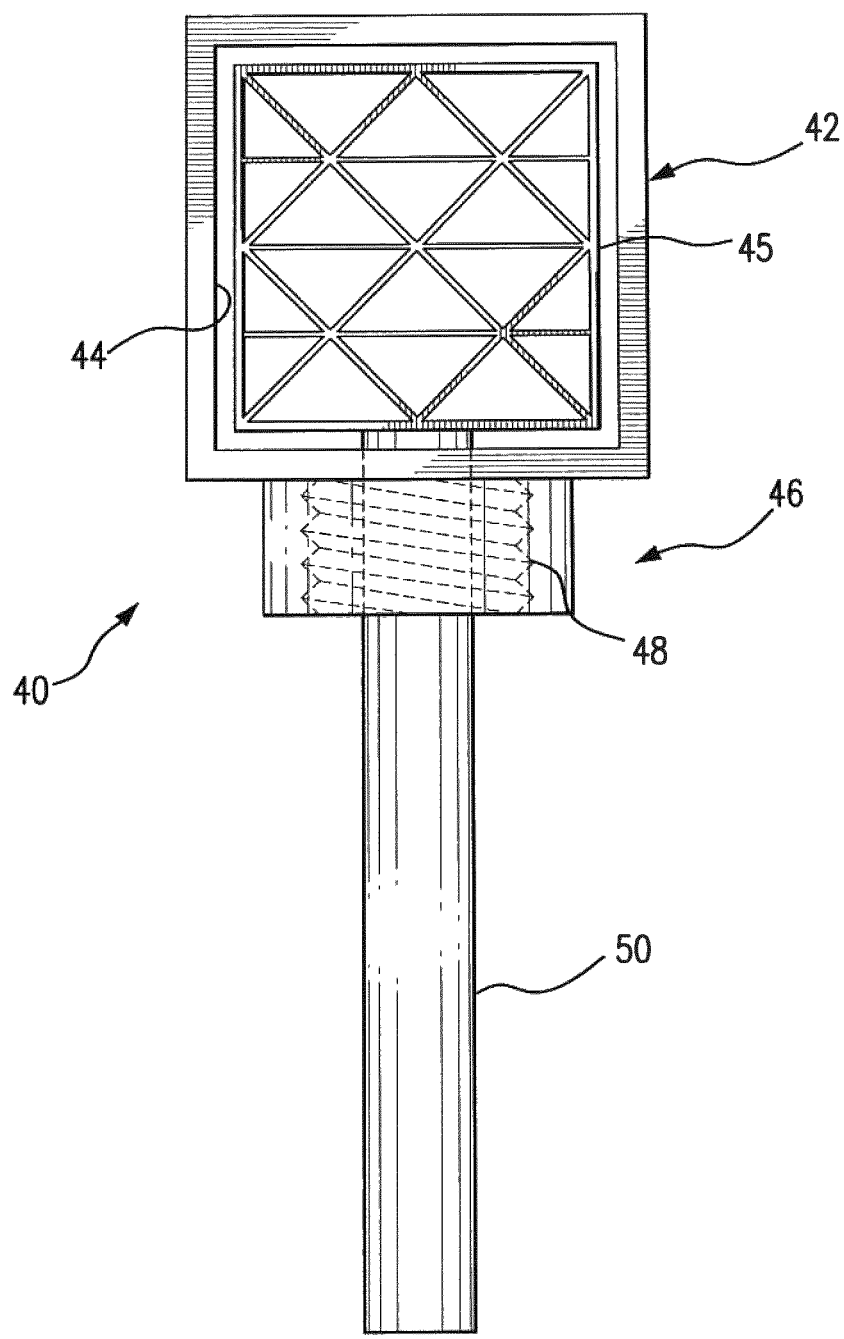
FIG. 3 is a front view of the assembly and combination illustrating an embodiment of the emanator element as being corrugated and attached to a wick.

The preferred embodiment of the invention is a device for evaporating and dispensing a volatile liquid. This device includes a number of particular components, including: a liquid reservoir containing an active volatile liquid or liquid composition; an emanator element housed within a tube through which air can be blown; a wicking element in the form of a wick or capillary that transfers the active volatile liquid from the reservoir to the emanating surface of the emanator element; and a blower or fan that is oriented so that the air produced is directed into the tube and passes over the surfaces of the emanator element.

The term "active volatile liquid" or "volatile liquid" is used to mean here a liquid which is at least partially volatile, i.e., can evaporate, and which is able to impart a fragrance or other benefit to the surrounding space. By "non-aqueous active volatile liquid composition" what is meant is an active volatile liquid composition which is essentially devoid of or contains only marginal amounts of water, e.g., one may cite as example a composition which contains less than 5%, of it total weight, of water. A useful active composition is also surfactant free or devoid of the latter. The emanator element is preferably provided in a body member which together form an assembly. To vaporize the volatile liquid, the emanator element has high surface area, while its open structure facilitates air flow therethrough. The element is positioned and supported by a body member that includes a tubular portion having an interior wall such that the emanator element is either spaced from the interior wall of the latter or lodged inside said tubular portion section and possibly fixed to the interior wall thereof without any spacing there-between.

The tubular portion is configured as an elongated passage that supports and retains the emanator element therein and defines a path for the air flow so that it comes in intimate contact with the entire open structure of the element. FIGS. 1 and 2 illustrate an assembly 10 having a body member in the form of a cylindrical tube 20 within which is located emanator element 24. The element 24 has an outer cylinder 24a and an internal configuration of filter paper folded in a four-pointed star shape 24b to provide the high surface area for vaporization of the volatile liquid. The element 24a comprises a sheet formed into a hollow cylinder of diameter 2.3 cm (circumference=7.2 cm) and a length of 5.0 cm: this has a surface area on all sides of the sheet (inner and outer surfaces of the cylinder) of 72 cm$^2$. The four-pointed star 24b is formed from a sheet measuring 7.2 cm×5 cm which is folded into the star shaped form: this also has a surface area on all sides of the sheet of 72 cm$^2$. Thus the total surface area of the emanator element 24 is 144 cm$^2$.

The tube 20 has an interior wall 22 and the emanator element 24 is spaced from the wall by ribs 25. The element 24 also has a wicking member 30 associated therewith. The wicking member 30 is designed to extend from the element 24 into a supply of volatile liquid in a reservoir as disclosed herein. The emanator element 20 includes a reservoir engaging portion 26 having internal screw threads 28 for engaging mating screw threads of the reservoir.

FIG. 3 illustrates an alternative embodiment of an assembly 40 wherein the tube 42 is rectangular in shape and has interior walls 44 that include therein a rectangular emanator element 45 in the form of folded paper having various triangular openings for passage of air. Again, the folds provide the desired high surface area for vaporization of the volatile liquid, and the wicking element 50 contacts the liquid in the reservoir. The emanator element 42 also includes a reservoir engaging portion 46 having internal screw threads 48 for engaging mating screw threads of the reservoir. The total surface area of this embodiment is approximately 176 cm$^2$.

Figure 4:
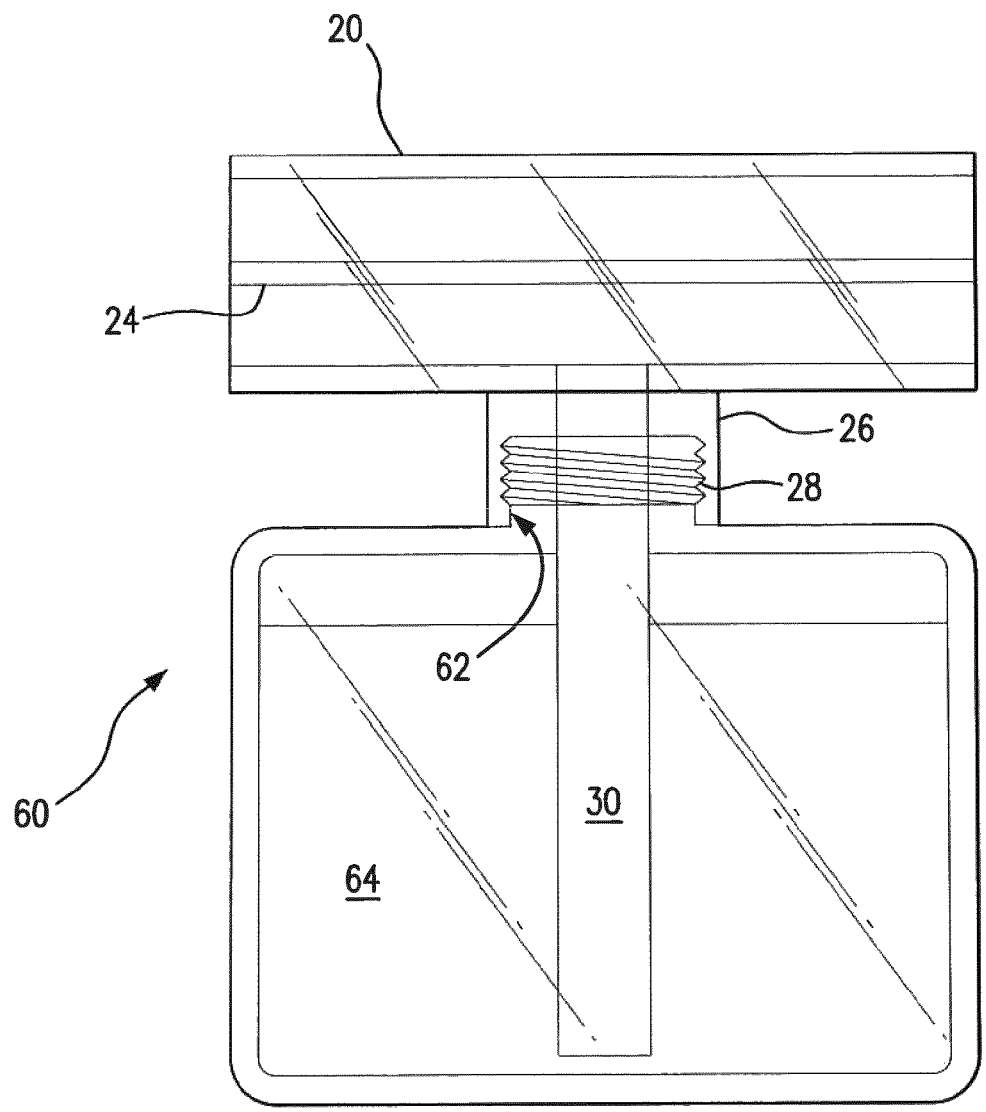
FIG. 4 is a side cross sectional view of the assembly of FIG. 1 threadedly engaged with a volatile liquid reservoir.

FIG. 4 shows the assembly of FIG. 1 connected to reservoir 60 by portion 26 threadedly engaged with reservoir outlet 62. Volatile liquid is shown as 64.

Preferably, the tubular portion is a cylindrical or polygonal tube having a cross-sectional area when viewed along its central axis of between 1 cm$^2$ and 20 cm$^2$; and more preferably between 2 cm$^2$ and 10 cm$^2$. The length of the tube is typically between 1 cm and 10 cm; more preferably between 2 cm and 6 cm. A straight, unbent tube is preferred to avoid pressure drops or other air flow restrictions as the air passes therethrough.

The emanating element typically has a surface area of between 50 cm$^2$ and 400 cm$^2$; more preferably between 80 cm$^2$ and 300 cm$^2$; more preferably between 100 cm$^2$ and 200 cm$^2$. The element is made of one or more sheets folded or otherwise arranged in a minimized volume to maximize surface area in a minimum amount of space. The thickness of these sheets is a function of the amount of active volatile that is to be absorbed within the emanating element, the overall surface area of the emanating element; and its porosity or pore-volume. In practice, the thickness of the sheets falls between approximately 0.2=a and 2 mm, more usually between 0.4 mm and 1 mm. Ideally the emanating element is oriented parallel to the central axis of the tube. The emanator element is fixed in position in the tube and neither the tube nor the emanator element are movable with respect to the volatile liquid reservoir or to each other.

Figure 9:
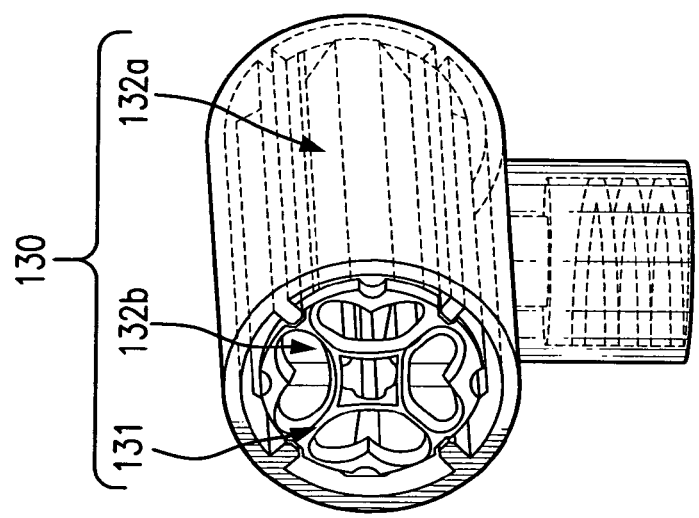
FIG. 9 is a perspective view of the emanator assembly of FIG. 8.
Figure 8:
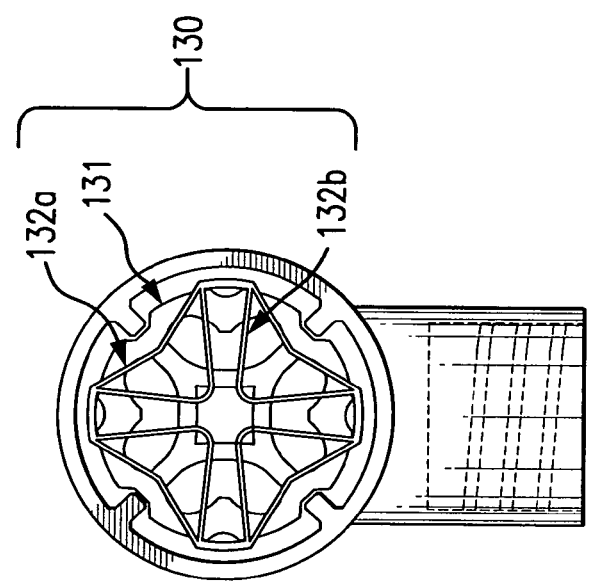
FIG. 8 is a front view of an embodiment of the emanator assembly that comprises emanator elements supported by a frame located within a cylindrical tube. The tube includes a thread on the engaging portion for engaging mating threads of a suitable reservoir.

For certain materials, the thickness of the emanator element is sufficient to enable it to retain its structure, weight and/or position in the tube. When less rigid or non self-supporting materials are used, the tube includes ribs 25 as shown in FIG. 1 or other spacing elements arranged around the interior wall to prevent the emanator element from contacting, lying upon or abutting large areas on the interior wall which in turn would obstruct or prevent air from flowing between the element and the wall and/or through the element itself if its structure were deformed. This assures that the air will flow around all portions of the element for maximal removal of the evaporated volatile liquid or fragrance. In other instances it may be desirable for the emanator element to be supported by a frame as shown in FIGS. 8 and 9. The frame holds the emanator element in the desired shape, and aids its location in the tube.

The rate at which liquid in the reservoir is transferred to the emanating element by the wick or capillary should be fast enough to ensure that the liquid is absorbed into the entire structure and across the entire surface of the emanating element. This occurs until the liquid in the reservoir has been exhausted. Thus, the full surface of the emanating element is constantly wetted or possibly even saturated throughout the use of the device for as long as there liquid in the reservoir.

The amount of liquid absorbed in the emanating element should be between 10% by weight and 30% by weight of the original amount of liquid in the reservoir; more preferably between 12% by weight and 25% by weight of the original amount of liquid in the reservoir; more preferably between 14% by weight and 20% by weight of the original amount of liquid in the reservoir. These calculations are based on the net amount of liquid in the device (i.e., in both the reservoir and wick) at the beginning of use of product, generally at the point of sale or before activation or engagement of the wick and the volatile liquid.

The amount of liquid absorbed in the wick or capillary should be between 0.5% by weight and 15% by weight of the original amount of liquid in the reservoir; more preferably between 2% by weight and 10% by weight of the original amount of liquid in the reservoir; more preferably between 4% by weight and 7% by weight of the original amount of liquid in the reservoir. Again, these calculations are based on the net amount of liquid in the device at the beginning of use of product. While one wick is illustrated herein, the invention contemplates the use of multiple wicks for withdrawing fluid from the reservoir and directing it to the emanating element.

The emanating element can be made of any one or more of a variety of materials. Suitable porous materials for the emanating element include: cellulose filter paper; cellulose board; non-woven materials such as spun-bound polyester or spun-bound polypropylene; sintered plastics; and porous or unglazed ceramics. Combinations can be used although these are not necessarily required. Preferably, sheet type materials are preferred as they can be folded or otherwise configured as noted to maximize the surface area within the tube. The wicking member can also be made of any of the materials that are suitable for the emanator element. Typically, the wicking member is made of organic or inorganic materials. Examples for appropriate inorganic materials include porous porcelain materials, molded ceramics, glass fibers, or asbestos, in combination with a suitable binder such as, for example, gypsum or bentonite. It is also possible to prepare wicks from powdered mineral materials, such as, for example, clay, talc, kieselguhr, alumina, silica or the like, singly or in combination with, for example, wood flour, carbon powder, or activated carbon, using an appropriate glue. Organic materials include felt, cotton, pulp, woven and non-woven cotton fibers, synthetic fibers, cellulose derivatives, e.g., papers, and woven and non-woven sintered or porous plastics. Preferably, the wicking member and emanatory element are made of the same material.

The active volatile liquid should contain between 40% by weight and 100% by weight fragrance-chemicals or essential oils; more preferably between 60% by weight and 100% by weight fragrance-chemicals or essential oils. The balance of these formulations can include solvents, dyes, colorants, anti-oxidants, UV inhibitors, bittering agents, etc. as are generally known to skilled artisans. Any particular formulations can be tested for determining the optimum surface area of the emanator element and the wicking structures for delivering the formulation to it.

The net initial volume of liquid in the reservoir before activation should be between 6 ml and 40 ml; preferably between 10 ml and 25 ml; and more preferably between 12 ml and 21 ml. "Activation" is used herein to mean that the emanator element is placed in fluid association with the volatile liquid either through contact with the wick of by extending a portion of the emanator element into the volatile liquid. How the liquid is distributed will depend on the how the device is used. There are various ways to provide the device for use and for activating it:

i) Prior to activation all the liquid is contained in the reservoir; the wick and emanating element have no liquid. During activation the wick is inserted into the reservoir and transfers liquid to the emanating or emanator element.

ii) Prior to activation the liquid is contained in the reservoir and the wick is already inserted into the liquid and will absorb some of the liquid; the emanating element has no liquid. During activation the emanating element is brought into contact with the wick.

iii) Prior to activation the liquid is distributed throughout the reservoir, wick and emanating element but is prevented from evaporating. During activation the means of preventing evaporation is removed.

The reservoir is usually a bottle that includes the volatile liquid therein. When provided to the purchaser, the bottle includes a cap to retain the volatile liquid therein. Typically a conventional screw cap (not shown) is provided for ease of removal and for securely retaining the volatile liquid therein.

The reservoir has the function of storing the non-aqueous active volatile liquid composition, from now on referred to also as "active composition", that is not absorbed by the wick and emanator element. The reservoir lid has the function of preventing the evaporation of the active composition from the reservoir. In particular, the reservoir lid securely covers the open end of the reservoir chamber by acting as, e.g., a screwed stopper. Suitable materials for the reservoir and lid include injection or thermoform molded materials such as those obtainable from polymers like polyethylene, polypropylene, polystyrene, polyvinyl chloride, polyvinyl acetate, polyamide, polyacrylamide, polymethylacrylate, and the like. Alternatively, the reservoir could be formed from glass. It is also understood that the reservoir and the lid could be parts of a single body. An example of such body can be a bottle having an open neck, the bottle being the reservoir and the neck being the lid.

Figure 5:
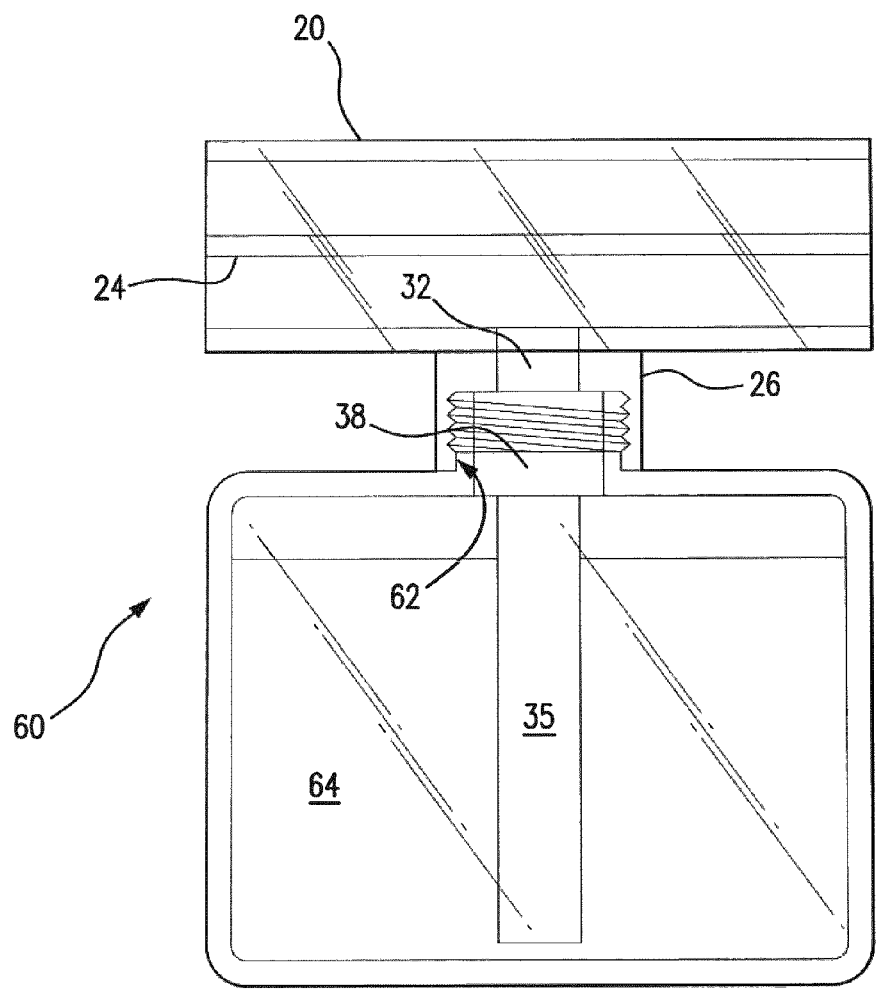
FIG. 5 is a side cross sectional view of a variation of the assembly of FIG. 1 illustrating different wicking members.

The wicking element can be provided in a number of ways, as shown in FIG. 5. Wick 35 can be provided in the bottle with a plug 38 or other bottle neck engaging portion provided so that the top of the wick is accessible to the emanator element. The wicking element can extend upward to the emanator element 24 to deliver liquid thereto when portion 26 is threadedly engaged with reservoir outlet 62. Alternatively, the emanator element can include the wicking member 30 as a portion or extension which extends into the bottle and to the volatile liquid as shown in FIGS. 1, 2 and 4. Another arrangement is shown in FIG. 5 by the dotted line wherein the emanator element 24 includes a short downwardly extending wicking portion 32 that extends to the bottle opening where it can contact the wicking member that is present in the bottle to provide a path for the volatile liquid to pass into the emanator element.

To prevent contact of the emanator element and volatile liquid before activation, the assembly and bottle can be provided separately, so that the removal of the cap and the screw attachment of the assembly to the bottle activates the device. Alternatively, other designs can be considered where the assembly is provided on the bottle without a cap but with a foil or other hermetically sealing member that prevents contact of the wicking member and liquid prior to activation. For this, the user simply removes the assembly and removes the foil so that the emanator element can contact the liquid through the wicking member.

As noted, the assembly can be used with a fan or blower to direct air into the tube and past the emanator element. The fan or blower can be powered by an AC supply or by batteries. The air moved by the fan or blower is directed into the tube by configuring the outlet of the blower to conform to the inlet of the tube. The velocity of the air traveling through the tube should be from 0.05 m/s to 1 m/s; more preferably from 0.1 m/s to 0.6 m/s, and these can be easily achieved by conventional fans and blowers.

Due to the high surface area of the emanator element and its confined arrangement inside of the tube, a high degree of control over the dispersing of the fragrance can be achieved. In the normal operation, the fan runs continuously while the emanator element is continuously provided with volatile liquid from the reservoir. This enables the device to provide a linear release of evaporated liquid or fragrance while controlling volatility so that the device can operate uniformly for an extended period of time until all of the liquid is removed from the reservoir. Most of the liquid is evaporated but a small amount may remain in the emanator element.

The emanator element is preferably designed to be used once and then be discarded after the reservoir is depleted. It is possible, however, when the same type of volatile liquid is to be dispersed to reuse the element a finite number of times, e.g., 2 or 3 times. Of course, if a different fragrance or volatile liquid is to be dispensed, a new element and assembly should be used. The fan or blower is directional in that it urges air movement through the tube past most or all of the evaporating liquid. This is achieved with a minimum application of energy as the tube is straight and without restrictions therein while also concentrating the air flow adjacent and around the emanator element. Thus, the present invention provides a combination of air flow and surface area for optimum dispensing of the fragrance or evaporated liquid. In particular, control is provided over the entire surface area of the emanator element to concentrate and provide maximum aeration of the fragrance in the tube and then out to the surrounding environment.

As noted, the continued use of the fan or blower disperses the fragrance for as long as the reservoir contains liquid. If the device is to be used in a small room, this could provide too much fragrance than is optimally desired. To provide further control over the amount of fragrance to be dispensed, the fan or blower device preferably features a circuit board that controls the blower on and off time. By periodically turning the blower motor on and off, a lesser amount of fragrance can be dispersed. While a variable speed blower can be used, this is a more complicated component that would increase the overall cost of the device. By a simple on-off sequencing of the motor, the same reduced dispensing rate of fragrance can be attained. Preferably the blower is functioning for between 5% and 50% of the time; more preferably between 10% and 30% of the time. For example, the blower can be turned on for 3 to 30 seconds and preferably between 6 and 18 seconds, and then be shut off for 30 to 57 seconds and preferably between 42 and 54 seconds.

Figure 10:
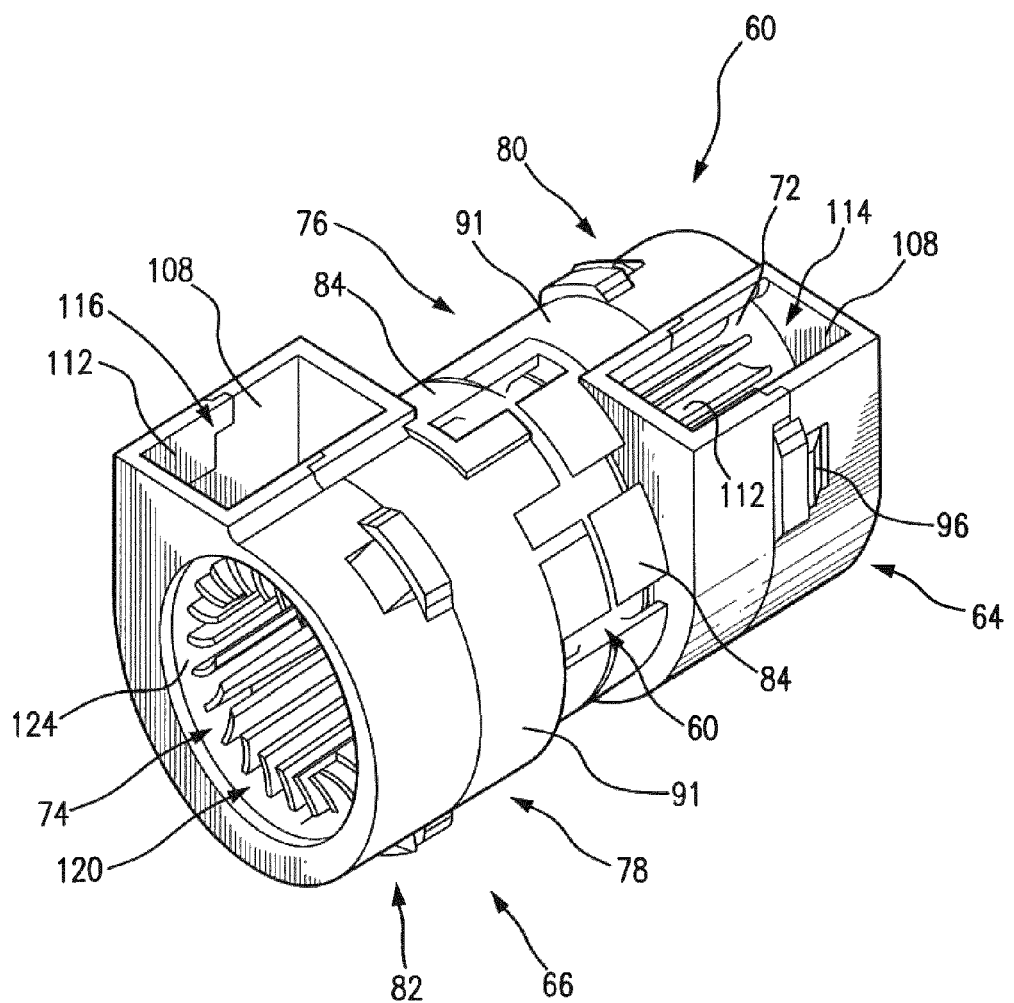
FIG. 10 is a view of a particular blower component for use in the present invention.

FIGS. 6-10 disclose a preferred fragrance dispensing device 100 that includes two emanator assemblies 105, 110 attached to volatile liquid reservoirs 115, 120, respectively. For clarity, the emanator sub-assemblies are removed from FIGS. 6 and 7 to more clearly show the spacing ribs 125. FIGS. 8 and 9 disclose assembly 105/110 with the emanator sub-assembly (130) in-place. The emanator sub-assembly comprises a frame (131) that supports the emanating elements (132a and 132b); orients the emanating elements parallel to the central axis of the tube; and, allows air to flow around all portions of the emanating elements. After activation of the wicking elements, these combinations are placed upon a support 130 in front of a dual blower component 60. The blower component has two blowers with exits that are positioned such that substantially all of the blown air from each blower passes through the body member of the respective assemblies 105, 110 to carry the evaporated volatile fluid out of the body members and into the surrounding environment. The details of the blower component 60 are described in US patent publication 2010/0044468. FIG. 10 of the present application is a perspective view of the dual blower component as per FIG. 8 of the '468 publication and the various elements of the dual centrifugal blower are represented in FIG. 10 of the present application by exactly the same numbers as disclosed in FIG. 8 of that document. The latter represents a perspective view of the same dual centrifugal blower also represented in FIG. 5 of the same document, and the numbered elements are more specifically disclosed in the relevant references to said numbered elements in paragraphs [0062] to [0080] of US 2010/0044468. The blower component cooperates with the two volatile fluid reservoirs and emanator elements to dispense either a greater amount of a single fragrance or two different fragrances into the surrounding environment. The disclosure of the '468 application is expressly incorporated herein by reference thereto for a more complete disclosure of the preferred dual blower of the invention. Of course, the present invention is operable using a single blower or fan of any type with a single emanator element and assembly.

Figure 16:
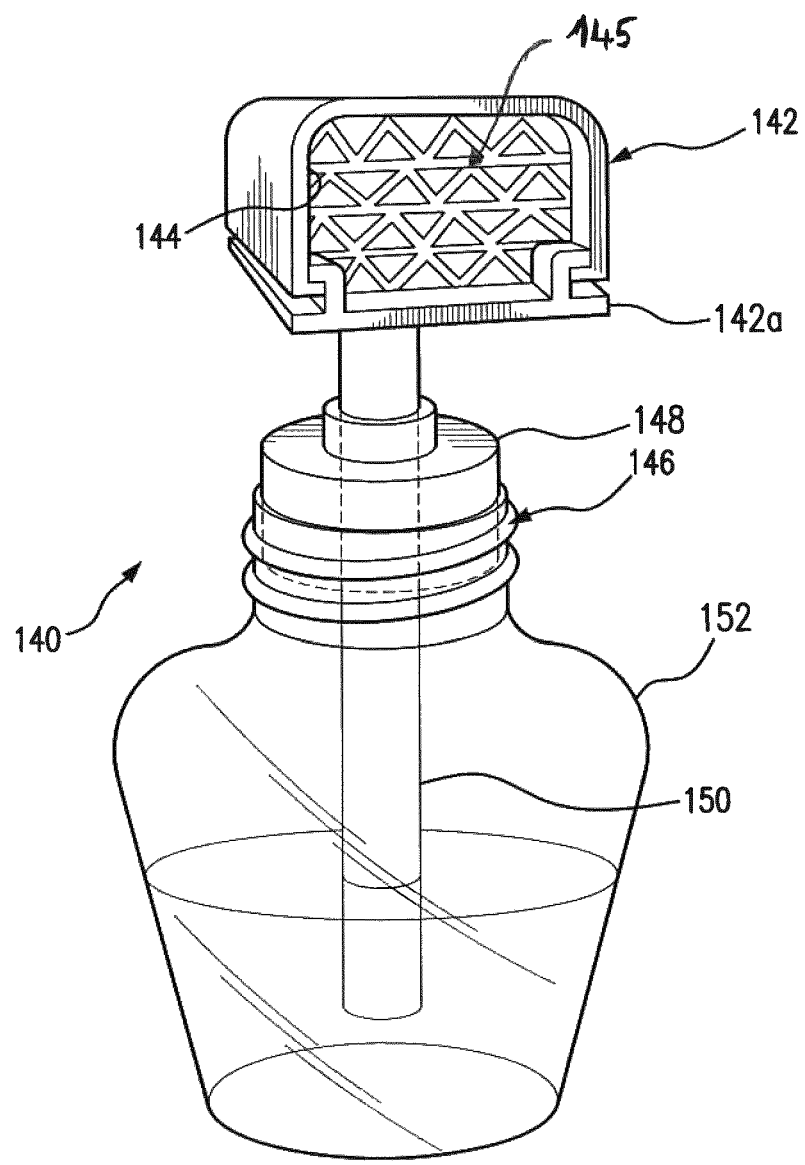
FIG. 16 is a front view of the assembly and combination illustrating an embodiment of the emanator element as being corrugated and attached to a wick.

FIG. 16 illustrates an alternative embodiment of an assembly 140 that includes a rectangular, two piece tube 142 that is fit together with a snap locking configuration. This tube 142 includes therein a rectangular emanator element 145 in the form of folded, bent or corrugated elements having various triangular openings for passage of air. Unlike the assemblies shown in FIGS. 1-5, the emanator element 145 extends to and is supported by the interior walls 144 of the tube 142. As in the other embodiments, the folds provide the desired high surface area for vaporization of the volatile liquid, and the wicking element 150 is provided for contacting the liquid in the reservoir and for delivering it to the emanator element 142. This is typically accomplished providing an aperture or hole in the bottom part 142A of the emanator element 142 through which the wicking element 150 passes.

The assembly 140 of FIG. 16 differs from the specific embodiments of the other FIGs. because the wicking element 150 is mounted in a plug or stopper 148 that fits into the neck 146 of the volatile liquid containing reservoir, namely, bottle 152. This alternative design for attaching the assembly to the bottle can also be used in the embodiments of FIGS. 1-5 in place of the cap 26. The shape and size of the bottle is not of critical importance provided that the wicking element 150 is sized to extend to the bottom of the bottle and the bottle is sized to fit in position adjacent the blower that forces air past the emanator element 145.

And while a two part snap-locking rectangular tube is used to support the emanator element 145, this could also be replaced by a single piece extruded or molded tube without departing from the teachings of the invention. In that alternative arrangement, the tube 142 would include an aperture or hole that allows the wicking element 150 to enter into the tube 142 to contact the emanator element for vaporizing and dispensing of the volatile liquid.

Figure 6:
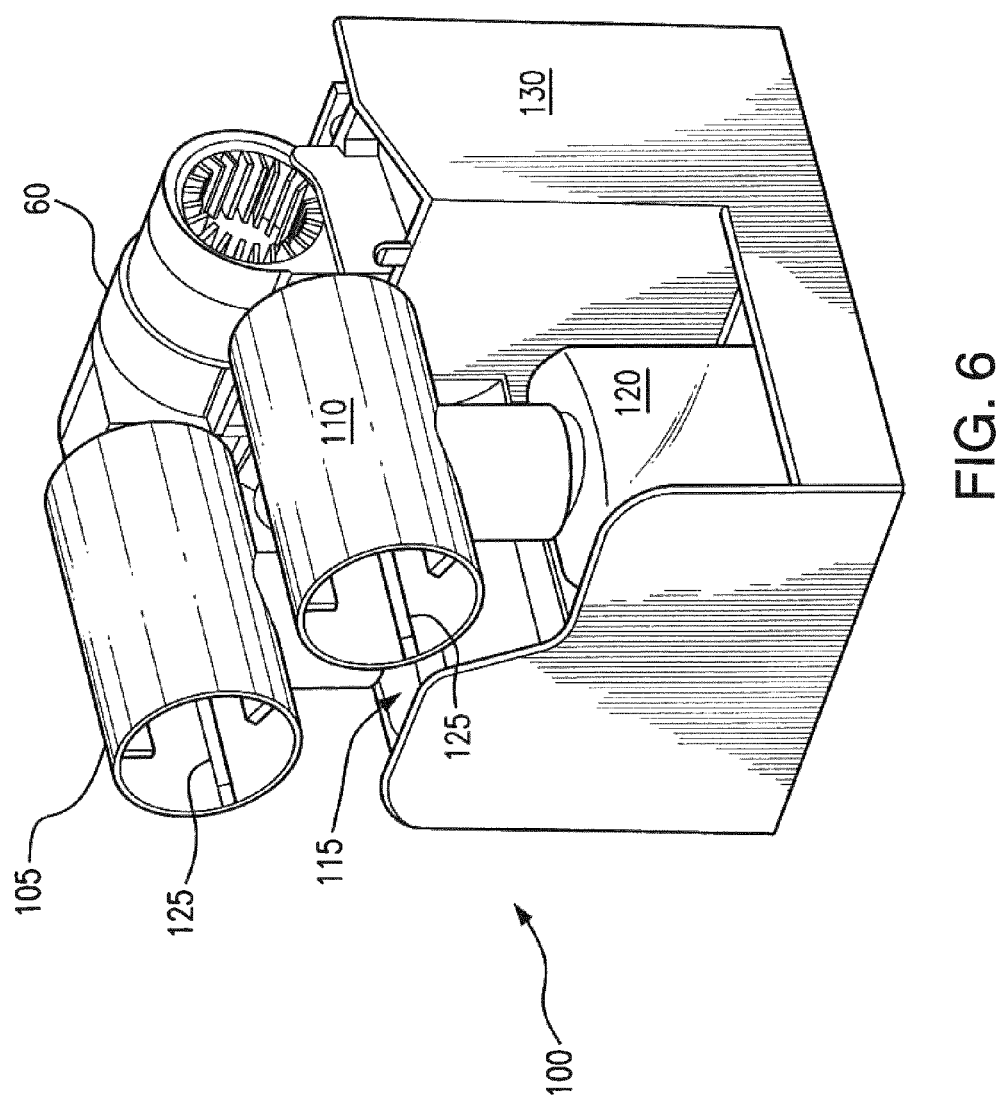
FIG. 6 is a front perspective view of a device that includes two assemblies each attached to a volatile fluid reservoir and placed adjacent a dual blower air moving component.
Figure 7:
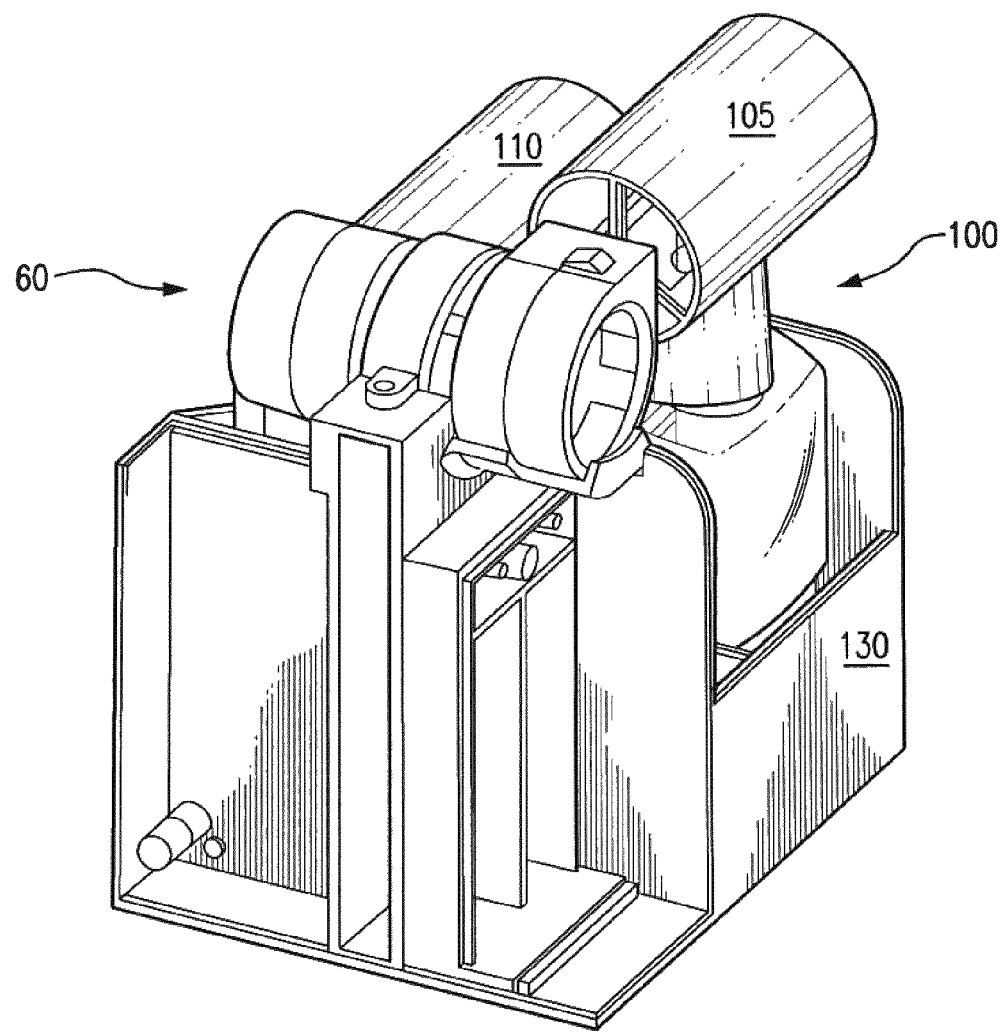
FIG. 7 is a rear perspective view of the device of FIG. 6.

Incidentally, the device of FIGS. 6 and 7 is shown with a preferred dual blower, but a less complicated device can be made using only a single blower for forcing air past or through a single emanator element of an assembly that is mounted on one bottle. The dual operation blower is preferred because it enables the user to diffuse the scents of different volatile liquids for enhanced olfactory experiences or, when a stronger single scent is desired, it can be used to diffuse the same scent from two bottles, thus doubling the olfactory perception of the scent. In many fragrancing situations, however, a single bottle and blower are quite suitable and acceptable.

The present invention does not require heat to disperse the fragrance. In particular, heating elements or components are not desired as they increase the energy requirements for operation, especially when the fan or blower is operated by a battery. Furthermore, due to the increased surface area and concentration of fragrance in the air stream that passes through the tube, additional evaporating by heating is not generally needed although it may be included for some embodiments, such as for dispersing the fragrance into a large area using a large reservoir of volatile liquid.

EXAMPLES

Example 1

The fragrance base composition detailed in Table 1 was prepared.

TABLE 1

| Ingredient Name | % w/w |
|---|---|
| Nonyl Acetate | 10.0 |
| Benzyl Acetate | 12.0 |
| Citronellyl Acetate | 6.0 |
| Phenylethyl Acetate | 10.0 |
| Cis-3-Hexenyl Acetate | 2.0 |
| Prenyl Acetate | 1.0 |
| Aldehyde Supra | 0.6 |
| Anethol | 1.0 |
| Applinate | 0.6 |
| Gamma Undecalactone | 4.0 |
| Delta Damascone [1)] | 0.8 |
| Dihydromyrcenol | 16.0 |
| DIPG Monomethyl Ether | 0.0 |

TABLE 1-continued

| Ingredient Name | % w/w |
|---|---|
| Dynascone ® [1] | 0.2 |
| Habanolide ® [1] | 1.0 |
| Hedione ® HC [1] | 3.0 |
| Indol @ 10% in DPG | 0.6 |
| Iralia ® Total [1] | 0.2 |
| Iso Eugenol Extra | 0.6 |
| Methoxymelonal | 0.4 |
| Oxane | 0.4 |
| Pelargene | 0.2 |
| Pelargodienal 1 DIPG | 0.6 |
| Cis-3-Hexenol | 2.0 |
| Polysantol ® [1] | 0.8 |
| Cis-3-Hexenyl Salicylate | 4.0 |
| Limonene | 4.0 |
| Verdox | 16.0 |
| Zestover | 2.0 |

[1] Origin: Firmenich SA, Geneva, Switzerland 10.0 g of the fragrance base composition was combined with 10.0 g of dipropylene glycol n-butyl ether (Dowanol® DPnB, origin: Dow Chemical Company) in the glass reservoir shown in Photograph E. A cylindrical polyester fiber wick measuring approximately 7 mm in diameter and 65 mm in length was inserted into the reservoir.

Figure 11:
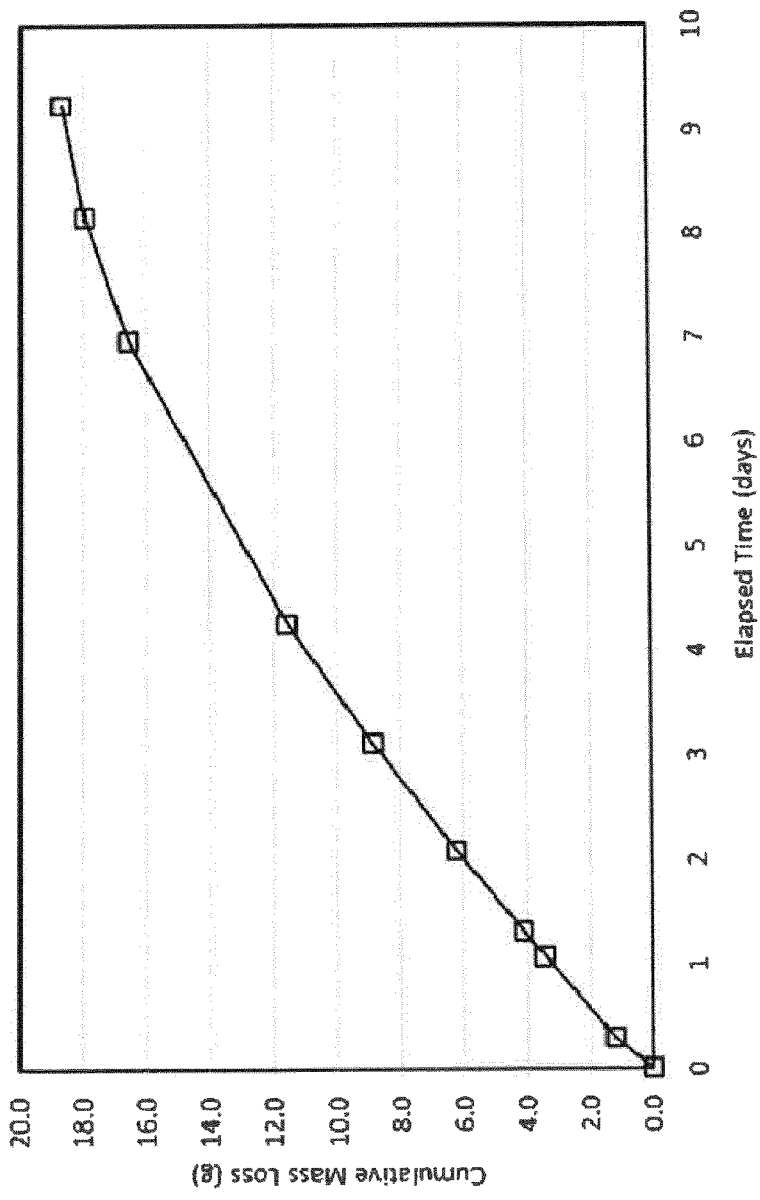
FIGS. 11 to 15 are graphs showing the mass of volatile active liquid composition released from the device over time, as measured by the loss of weight of the device, under controlled temperature/humidity conditions, and under a variety of operation conditions described in detail in Examples 1 to 5.
Figure 17:
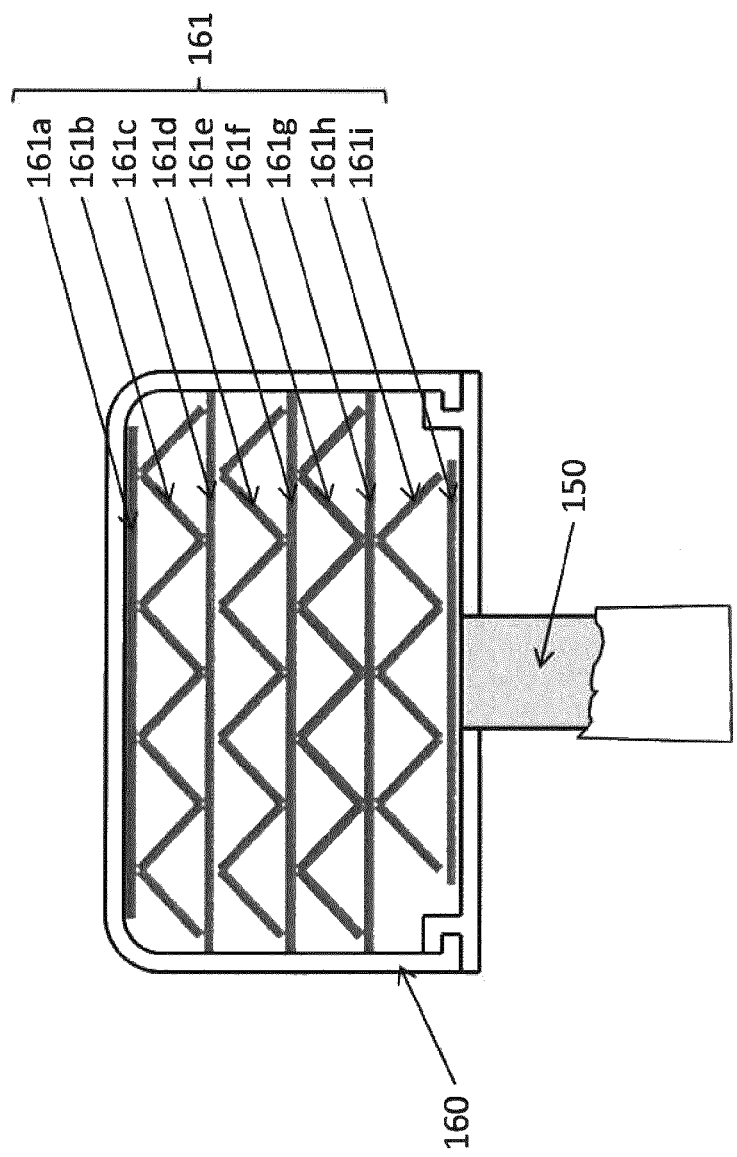
FIG. 17 is a sectional view of an embodiment of the emanator assembly that comprises a plurality of emanator components formed into a corrugated arrangement and contained within a tube of approximately rectangular section.

The emanator assembly shown in FIG. 11 and FIG. 17 was constructed using a 60 mm length of rectangular polypropylene conduit (160 in FIG. 17) with internal dimensions 18 mm×11 mm. The emanator element (161 in FIG. 17) was constructed using Whatman No. 4 qualitative filter paper (origin: Whatman plc). The emanator element comprised 9 separate components (161a to 161l in FIG. 17) in contact with one another. Emanator component 161a measured 13 mm×50 mm and was in contact with the inside bottom wall of the tube and in direct contact with the wick (150 in FIG. 17). Emanator component 161b measured 19 mm×50 mm and was folded into a corrugated form and was placed in contact with component 161a. Component 161c measured 18 mm×50 mm and was in contact with component 161b. Component 161d measured 25 mm×50 mm and was folded into a corrugated form and was placed in contact with component 161c. Component 161e measured 18 mm×50 mm and was in contact with component 161d. Component 161f measured 25 mm×50 mm and was folded into a corrugated form and was placed in contact with component 161e. Component 161g measured 18 mm×50 mm and was in contact with component 161f. Component 161h measured 25 mm×50 mm and was folded into a corrugated form and was placed in contact with component 161g. Component 161i measured 18 mm×50 mm and was in contact with component 161h and in contact with the inside top of the tube 160.

Air was blown through the tube by a centrifugal blower component shown in more detail in FIG. 10 connected to a 3V supply running continuously. The emanator assembly was positioned so that the air exiting the blower passed through the rectangular tube. The total emanator assembly surface area in contact with air stream was approximately 162 cm$^2$.

The total mass of the liquid composition, the reservoir, the wick and the emanator assembly was recorded. The device was then placed in a temperature/humidity controlled test room and its weight recorded at regular time intervals thereafter. The data recorded is given in Table 2 and is shown graphically in FIG. 11.

TABLE 2

| Elapsed Time (days) | Total Mass (g) | Cumlative Mass Loss (g) | Cumlative Mass Loss (%) |
|---|---|---|---|
| 0.00 | 96.91 | 0.00 | 0.00 |
| 0.29 | 95.71 | 1.20 | 5.99 |
| 1.07 | 93.47 | 3.44 | 17.18 |
| 1.31 | 92.80 | 4.11 | 20.55 |
| 2.08 | 90.69 | 6.22 | 31.10 |
| 3.11 | 88.02 | 8.89 | 44.45 |
| 4.25 | 85.32 | 11.59 | 57.95 |
| 6.96 | 80.34 | 16.57 | 82.84 |
| 8.15 | 78.96 | 17.95 | 89.76 |
| 9.23 | 78.21 | 18.70 | 93.50 |

Example 2

Example 1 was repeated with the blower unit running in the opposite direction. This resulted in significantly lower air flow through the emanator assembly. The recorded data is given in Table 3 and shown graphically in FIG. 12.

TABLE 3

| Elapsed Time (days) | Total Mass (g) | Cumlative Mass Loss (g) | Cumlative Mass Loss (%) |
|---|---|---|---|
| 0.00 | 97.28 | 0.00 | 0.00 |
| 1.11 | 96.52 | 0.76 | 3.79 |
| 2.07 | 96.17 | 1.11 | 5.53 |
| 3.01 | 95.83 | 1.45 | 7.24 |
| 6.10 | 94.72 | 2.56 | 12.80 |
| 8.07 | 94.02 | 3.26 | 16.31 |
| 10.21 | 93.26 | 4.02 | 20.08 |
| 13.20 | 92.23 | 5.05 | 25.26 |
| 16.08 | 91.25 | 6.03 | 30.16 |
| 20.01 | 89.94 | 7.34 | 36.68 |
| 23.15 | 88.93 | 8.35 | 41.73 |
| 30.02 | 86.83 | 10.45 | 52.24 |
| 36.97 | 84.88 | 12.40 | 62.00 |
| 44.03 | 83.10 | 14.18 | 70.88 |

Figure 12:
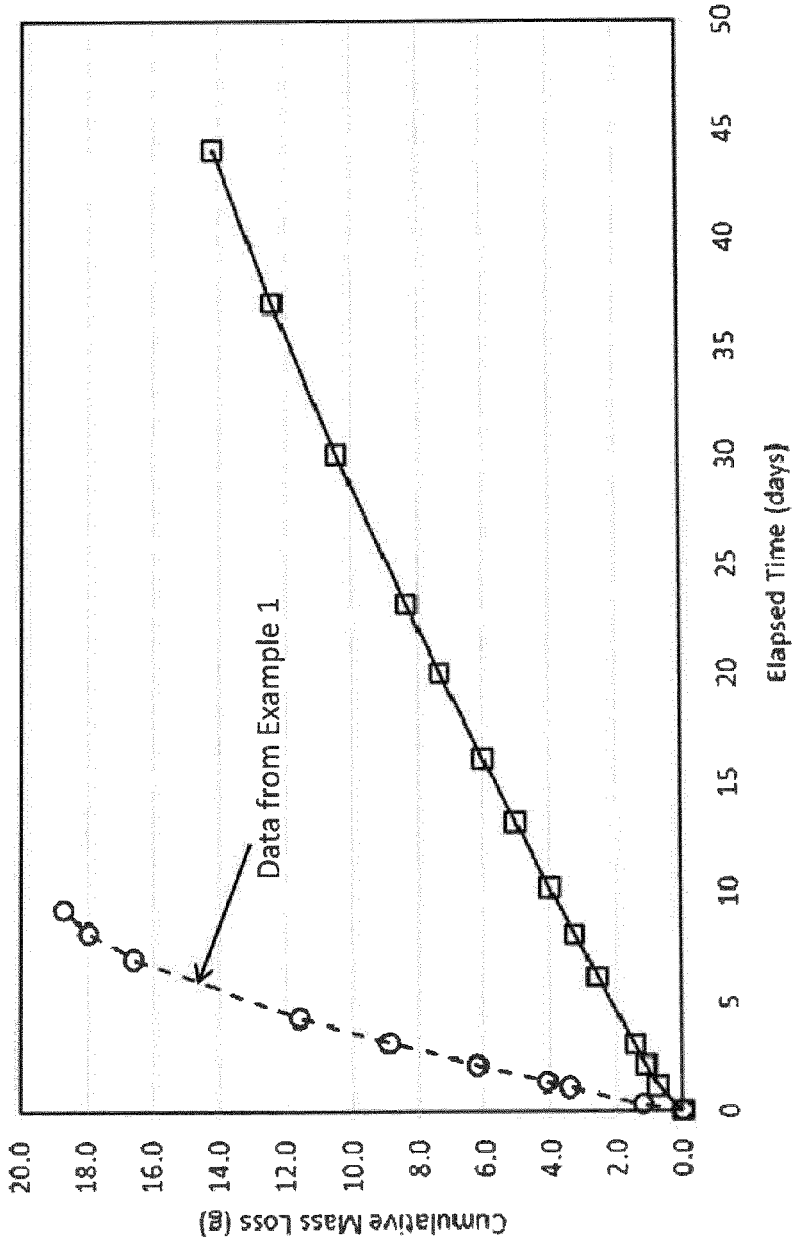

The data from Example 1, obtained in the same temperature/humidity control conditions, is included in FIG. 12 for comparison. It is evident that in this example when the centrifugal blower is operating in reverse the evaporation of volatile liquid composition is reduced by a factor of approximately 7 to 9.

Example 3

Example 1 was repeated but with the blower unit set to the "off" position, i.e. no air was entering the emanator assembly. The recorded data is given in Table 4 and shown graphically in FIG. 13.

TABLE 4

| Elapsed Time (days) | Total Mass (g) | Cumlative Mass Loss (g) | Cumlative Mass Loss (%) |
|---|---|---|---|
| 0.00 | 97.42 | 0.00 | 0.00 |
| 1.11 | 97.32 | 0.10 | 0.49 |
| 2.07 | 97.24 | 0.18 | 0.91 |
| 3.01 | 97.16 | 0.26 | 1.32 |
| 6.10 | 96.89 | 0.53 | 2.67 |
| 8.07 | 96.71 | 0.71 | 3.54 |
| 10.21 | 96.53 | 0.89 | 4.47 |
| 13.20 | 96.27 | 1.15 | 5.77 |

TABLE 4-continued

| Elapsed Time (days) | Total Mass (g) | Cumlative Mass Loss (g) | Cumlative Mass Loss (%) |
|---|---|---|---|
| 16.08 | 96.02 | 1.40 | 7.02 |
| 20.01 | 95.68 | 1.74 | 8.72 |
| 23.15 | 95.41 | 2.01 | 10.07 |
| 30.02 | 94.82 | 2.60 | 13.02 |
| 36.97 | 94.23 | 3.19 | 15.97 |
| 44.03 | 93.63 | 3.79 | 18.94 |

Figure 13:
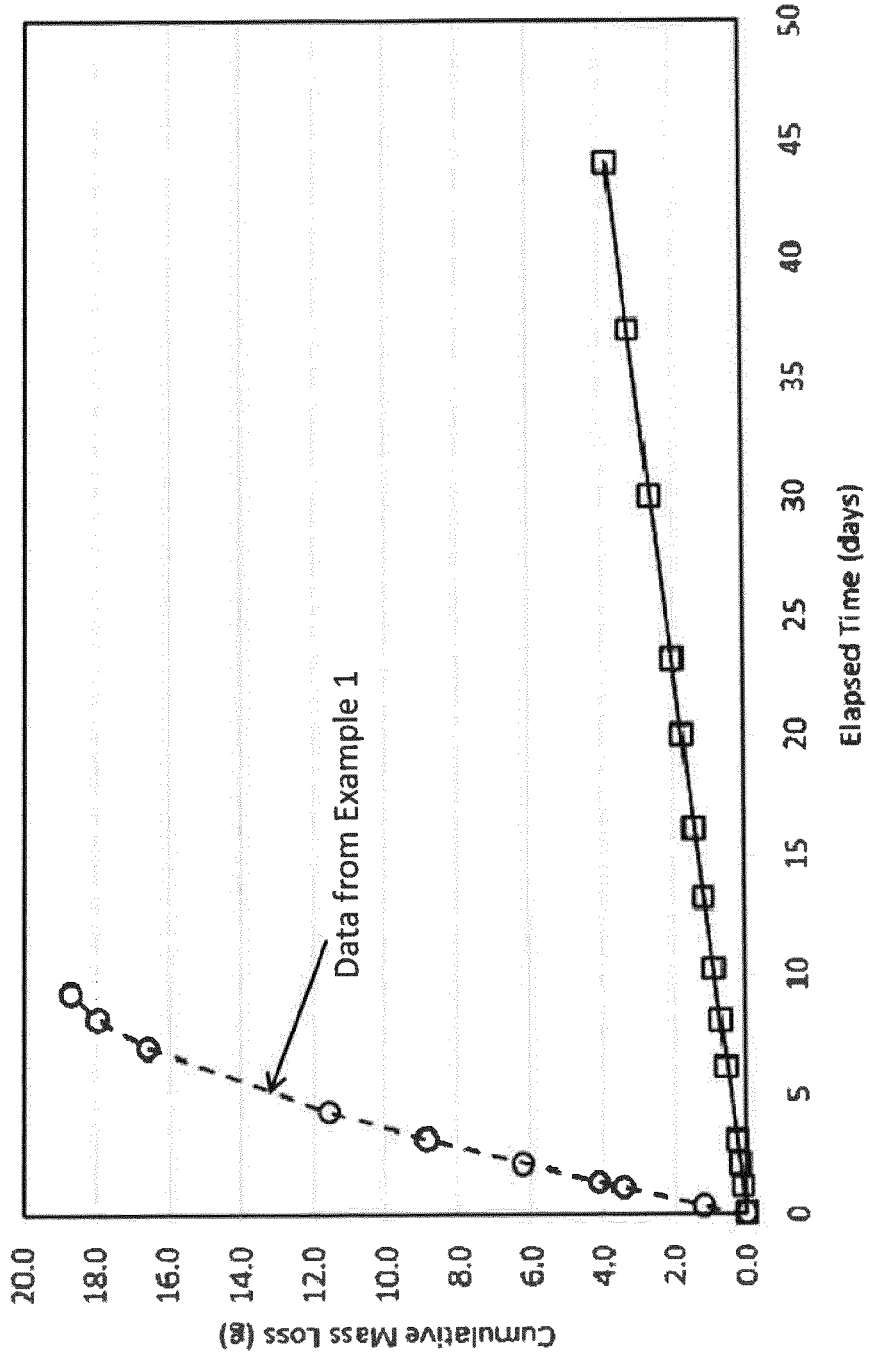

The data from Example 1, obtained in the same temperature/humidity control conditions, is included in FIG. 13 for comparison. It is evident that in this example when there is no air forced through the emanator assembly the evaporation of volatile liquid composition is reduced by a factor of approximately 30 to 40.

Example 4

10.0 g of the fragrance base composition detailed in Example 1 was combined with 10.0 g of dipropylene glycol n-propyl ether (Dowanol DPnP, origin: Dow Chemical Company) in the glass reservoir shown in FIG. 16. A cylindrical polyester fiber wick measuring approximately 7 mm in diameter and 65 mm in length was inserted into the reservoir. An emanator assembly identical to that described in Example 1 was prepared and placed on top of the wick so that the wick was in direct contact with the bottom component. Air was blown through the tube by a centrifugal blower component as shown in FIG. 10 connected to a 3V supply running continuously. The emanator assembly was positioned so that the air exiting the blower passed through the rectangular tube. The total emanator assembly surface area in contact with air stream was approximately 162 cm$^2$.

Figure 14:
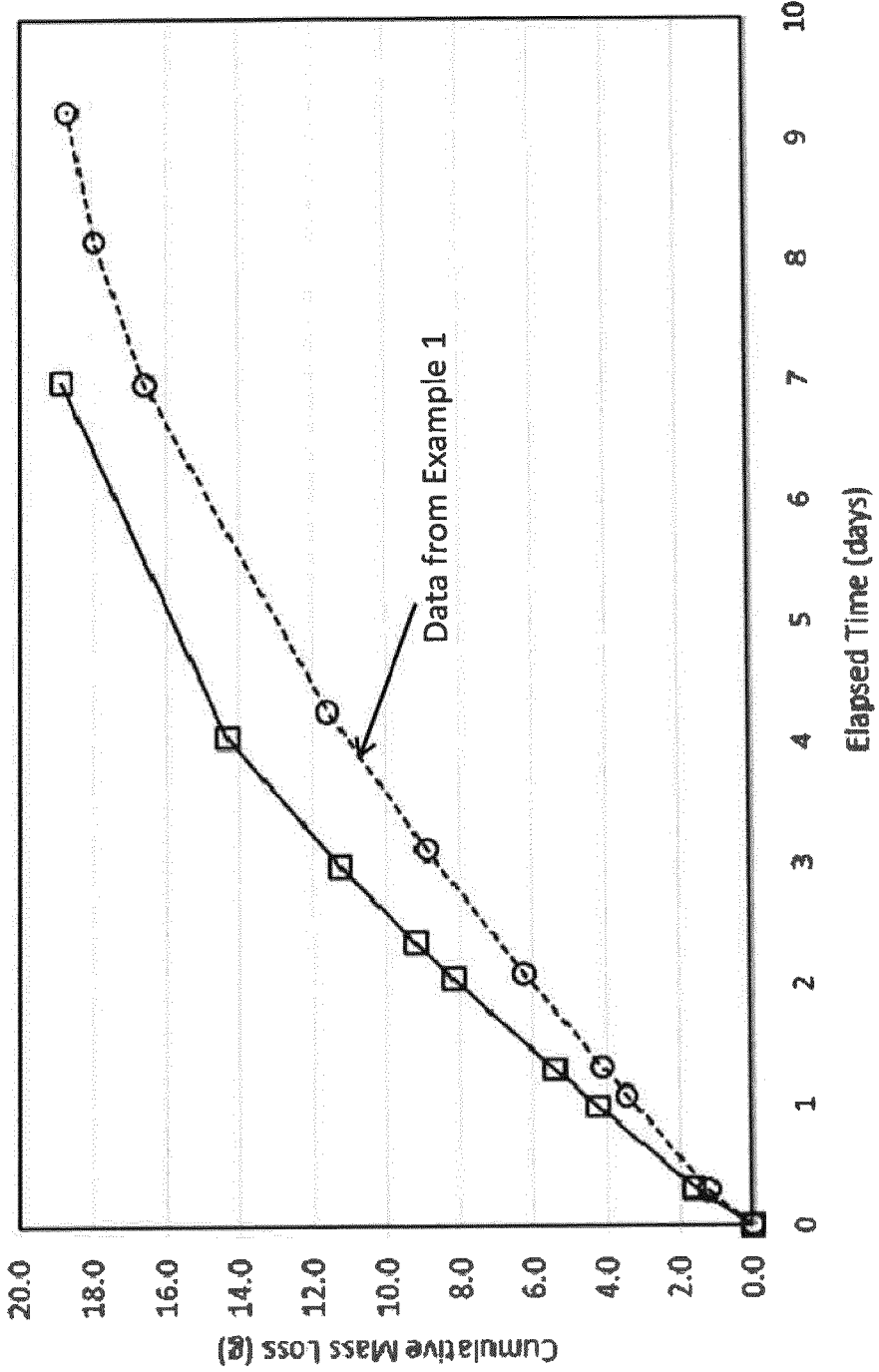

The total mass of the liquid composition, the reservoir, the wick and the emanator assembly was recorded. The device was then placed in a temperature/humidity controlled test room and its weight recorded at regular intervals thereafter. The data recorded is given in Table 5 and is shown graphically in FIG. 14. The data from Example 1, obtained in the same temperature/humidity control conditions, is included in FIG. 14 for comparison. The use of dipropylene glycol n-propyl ether in place of dipropylene glycol n-butyl ether increases the rate of evaporation of the volatile liquid composition.

TABLE 5

| Elapsed Time (days) | Total Mass (g) | Cumlative Mass Loss (g) | Cumlative Mass Loss (%) |
|---|---|---|---|
| 0.00 | 96.63 | 0.00 | 0.00 |
| 0.31 | 95.03 | 1.60 | 7.99 |
| 0.98 | 92.40 | 4.23 | 21.14 |
| 1.29 | 91.22 | 5.41 | 27.05 |
| 2.04 | 88.48 | 8.15 | 40.73 |
| 2.34 | 87.44 | 9.19 | 45.93 |
| 2.97 | 85.38 | 11.25 | 56.24 |
| 4.04 | 82.32 | 14.31 | 71.54 |
| 6.98 | 77.79 | 18.84 | 94.21 |

Example 5

10.0 g of the fragrance base composition detailed in Example 1 was combined with 10.0 g of dipropylene glycol n-propyl ether (Dowanol DPnP, origin: Dow Chemical Company) in a glass reservoir. A cylindrical polyester fiber wick measuring approximately 7 mm in diameter and 65 mm in length was inserted into the reservoir. The emanator assembly shown in FIG. 8 was attached to the reservoir by means of a threaded engaging portion, so that the wick passed through the engaging portion and contacted the emanating element. The emanating element was constructed from two rectangular sections of Nonwoven SVM90 (origin: BFF Nonwovens). One element (132a in FIG. 8) measured 69 mm×50 mm; the other element (132b in FIG. 8) measured 92 mm×50 mm. The elements were folded around the support frame (131 in FIG. 8.).

The reservoir and emanator assembly combination was positioned upon a support of the fragrance dispensing device of FIG. 6 such that substantially all of the blown air from one of the centrifugal blowers passed through the cylindrical tube of the emanator assembly. The total emanator element surface area in contact with the air stream was approximately 140 cm$^2$.

Figure 15:
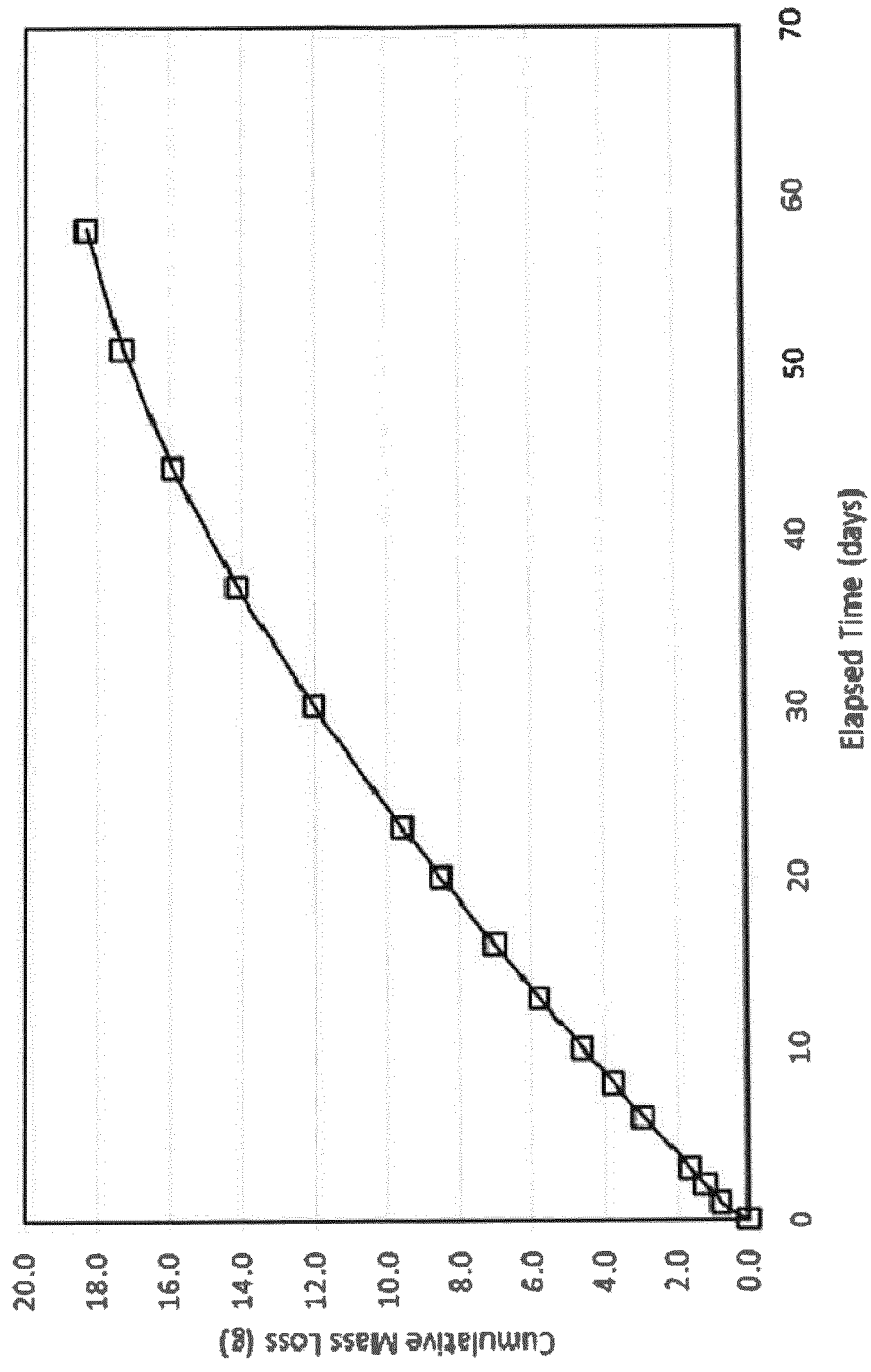

The fragrance dispensing device featured a circuit board that controlled the blower on and off time. The device was programmed so that the blower was turned on for 12 seconds, and then shut off for 48 seconds. The circuit board also allowed the direction of rotation of the centrifugal blower to be reversed. This was achieved by reversing the polarity of the electric current to the motor driving the blower. The device was programmed so that the direction of rotation was reversed every 30 minutes: thus for 30 minutes the centrifugal blower was rotating in a clockwise direction; and for 30 minutes the centrifugal blower was rotating in an anti-clockwise direction. When rotating in a clockwise direction the centrifugal blower generated an air flow at discharge of approximately 3.0 m/s; when rotating in an anti-clockwise direction the centrifugal blower generated an air flow at discharge of approximately 0.5 m/s. The corresponding air flow rates through the tube of the emanating assembly were approximately 1.2 m/s and 0.2 m/s respectively. The total mass of the liquid composition, the reservoir, the wick and the emanator assembly was recorded. The device was then placed in a temperature/humidity controlled test room and the weight recorded at regular intervals thereafter. The data recorded is given in Table 6 and is shown graphically in FIG. 15.

TABLE 6

| Elapsed Time (days) | Total Mass (g) | Cumlative Mass Loss (g) | Cumlative Mass Loss (%) |
|---|---|---|---|
| 0.00 | 105.94 | 0.00 | 0.00 |
| 0.97 | 105.17 | 0.77 | 3.85 |
| 2.01 | 104.72 | 1.22 | 6.09 |
| 2.98 | 104.31 | 1.63 | 8.17 |
| 5.98 | 103.04 | 2.90 | 14.52 |
| 8.00 | 102.19 | 3.75 | 18.75 |
| 10.03 | 101.35 | 4.59 | 22.93 |
| 12.98 | 100.16 | 5.78 | 28.90 |
| 16.08 | 98.94 | 7.00 | 35.02 |
| 20.04 | 97.43 | 8.51 | 42.56 |
| 22.96 | 96.36 | 9.58 | 47.91 |
| 30.09 | 93.92 | 12.02 | 60.09 |
| 37.05 | 91.83 | 14.11 | 70.57 |
| 43.97 | 90.06 | 15.88 | 79.40 |
| 51.00 | 88.64 | 17.30 | 86.51 |
| 58.06 | 87.63 | 18.31 | 91.53 |

The invention claimed is:
1. An assembly for evaporation and dispensing of a volatile liquid, comprising:

an emanator element having an open structure and high surface area between 50 cm² and 400 cm² and made of a material that is able to absorb and evaporate volatile liquids, the emanatory element configured to maximize surface area in a minimum space; and a body member that includes a tubular portion having an interior wall for receiving the emanator element therein, the tubular portion being in the form of a straight or unbent cylindrical or polygonal tube having a cross-sectional area when viewed along its central axis of between 1 cm² and 20 cm², with the body member receiving the emanator element therein to provide the high surface area of emanatory element within the tubular portion;

wherein the emanator element and body member being further configured and dimensioned to provide a space between the interior wall of the body member and the emanator element once the emanator element is received into the body member to allow air flow through the open structure of the emanator element as well as between the interior wall and the emanator element; and wherein the emanator element comprises one or more sheets having folds, corrugations, ripples or waves that are arranged to provide a maximum surface area of the emanatory element within the tubular portion.

2. The assembly of claim 1, wherein the body member includes a volatile fluid reservoir engaging portion surrounding a passage that extends from the engaging portion to the tubular portion.

3. An assembly according to claim 1, wherein said surface area is between 80 and 300 cm² or between 100 and 200 cm².

4. An assembly for evaporation and dispensing of a volatile liquid, comprising:

an emanator element having an open structure and high surface area between 50 cm² and 400 cm² and made of a material that is able to absorb and evaporate volatile liquids; and a body member that includes a tubular portion having an interior wall for receiving the emanator element therein;

wherein the emanator element and body member are configured and dimensioned to provide a space between the interior wall of the body member and the emanator element once the emanator element is received into the body member to allow air flow through the open structure of the emanator element as well as between the interior wall and the emanator element; and wherein the emanator element comprises one or more sheets folded or otherwise arranged in a minimized volume to maximize surface area within a minimum space;

wherein the emanator element comprises one or more sheets folded or otherwise arranged in the shape of a star located within a cylindrical tube, wherein the thickness of the sheet or sheets is between 0.2 mm and 2.0 mm or between 0.4 mm and 1.0 mm.

5. The assembly of claim 2, which further comprises a wicking element extending away from the emanator element and at least into the reservoir engaging portion.

6. The assembly of claim 1, wherein the emanator element includes folds or corrugations, ripples, waves or other folded arrangements and comprises cellulose filter paper, cellulose board, a non-woven material, a plastic or a porous or unglazed ceramic.

7. The assembly of claim 1, wherein the interior wall of the tubular portion includes internal ribs or spacers to position the emanator element away from the interior wall to allow air to flow between the wall and emanator element, with the space being sufficient to allow air flow therethrough, wherein air can also flow through the open structure of the emanator element thereby providing evaporation and dispensing of the volatile liquid.

8. A combination comprising the assembly of claim 1 and a reservoir of volatile liquid, which further comprises a wicking element extending from the emanator element into the volatile liquid and either being part of or associated with the emanator element or being associated with the reservoir; wherein one or more wicking elements can be present and the engaging portion optionally includes threads for engaging mating threads of the reservoir.

9. A device for evaporation and dispensing of a volatile liquid comprising:

the assembly of claim 1; and an air moving component operatively associated with the assembly for directing air flow though the tubular portion and around and through the open structure of the emanator element for carrying evaporated liquid volatiles out of the body member.

10. The device of claim 9, wherein the air moving component imparts a velocity of 0.05 m/s to 1 m/s to the air traveling through the tubular component.

11. The device of claim 9, wherein the air moving component comprises a fan or blower controlled by a circuit board that provided on and off times wherein the fan or blower is on and providing air movement for between 5% and 50% of the time.

12. A method of evaporating and dispensing of a volatile liquid from a reservoir, which comprises:

providing the combination of claim 8;

associating the wicking element with both the emanator element and the volatile liquid so that the volatile liquid is absorbed into and across the entire surface of the emanating element; and directing air flow though the tubular portion and around and through the open structure of the emanator element for carrying evaporated liquid volatiles out of the body member.

13. The device of claim 10 wherein the air moving component comprises a fan or blower controlled by a circuit board that provided on and off times wherein the fan or blower is on and providing air movement for between 5% and 50% of the time.

14. A method of evaporating and dispensing of a volatile liquid from a reservoir, which comprises:

providing the device of claim 9;

associating the wicking element with both the emanator element and the volatile liquid so that the volatile liquid is absorbed into and across the entire surface of the emanating element; and directing air flow though the tubular portion and around and through the open structure of the emanator element, preferably by the air moving component, for carrying evaporated liquid volatiles out of the body member.

15. A method of evaporating and dispensing of a volatile liquid from a reservoir, which comprises:

providing the device of claim 10;

associating a wicking element with both the emanator element and the volatile liquid so that the volatile liquid is absorbed into and across the entire surface of the emanating element; and directing air flow though the tubular portion and around and through the open structure of the emanator element, preferably by the air moving component, for carrying evaporated liquid volatiles out of the body member.

16. A method of evaporating and dispensing of a volatile liquid from a reservoir, which comprises:
    providing the device of claim 11;
    associating a wicking element with both the emanator element and the volatile liquid so that the volatile liquid is absorbed into and across the entire surface of the emanating element; and
    directing air flow though the tubular portion and around and through the open structure of the emanator element, preferably by the air moving component, for carrying evaporated liquid volatiles out of the body member.

17. The assembly of claim 4, wherein the interior wall of the tubular portion includes internal ribs or spacers to position the emanator element away from the interior wall to allow air flow between the wall and emanator element.

18. The method of claim 12 wherein the air flow is directed by an air moving component.

19. An assembly for evaporation and dispensing of a volatile liquid, comprising:
    an emanator element having an open structure and high surface area between 50 cm$^2$ and 400 cm$^2$ and made of a material that is able to absorb and evaporate volatile liquids; and
    a body member that includes a tubular portion having an interior wall for receiving the emanator element therein;
    wherein the emanator element and body member are configured and dimensioned to provide a space between the interior wall of the body member and the emanator element once the emanator element is received into the body member to allow air flow through the open structure of the emanator element as well as between the interior wall and the emanator element; and
    wherein the emanator element comprises one or more sheets folded or otherwise arranged in a minimized volume to maximize surface area within a minimum space;
    wherein the emanator element is rectangular in shape and has interior walls that include various triangular openings for the passage of air wherein the thickness of the sheet or sheets is between 0.2 mm and 2.0 mm or between 0.4 mm and 1.0 mm.

20. An assembly for evaporation and dispensing of a volatile liquid, comprising:
    an emanator element having an open structure and high surface area between 50 cm$^2$ and 400 cm$^2$ and made of a material that is able to absorb and evaporate volatile liquids; and
    a body member that includes a tubular portion having an interior wall for receiving the emanator element therein;
    wherein the emanator element and body member are configured and dimensioned to provide a space between the interior wall of the body member and the emanator element once the emanator element is received into the body member to allow air flow through the open structure of the emanator element as well as between the interior wall and the emanator element; and
    wherein the emanator element comprises one or more sheets folded or otherwise arranged in a minimized volume to maximize surface area within a minimum space;
    wherein the emanator element has an irregular tube shape with inwardly directed triangular portions wherein the thickness of the sheet or sheets is between 0.2 mm and 2.0 mm or between 0.4 mm and 1.0 mm.

* * * * *

UNITED STATES PATENT AND TRADEMARK OFFICE
CERTIFICATE OF CORRECTION

PATENT NO. : 9,457,117 B2  
APPLICATION NO. : 13/981665  
DATED : October 4, 2016  
INVENTOR(S) : O'Leary et al.

Page 1 of 1

It is certified that error appears in the above-identified patent and that said Letters Patent is hereby corrected as shown below:

On the Title Page:
Item (73) Assignee, after "Firmenich SA, Geneva (CH)", add -- Momentum Industries, Inc., Fort Wayne, IN (US) --.

Signed and Sealed this  
Eighth Day of November, 2016

Michelle K. Lee  
*Director of the United States Patent and Trademark Office*